United States Patent
Gattupalli et al.

(10) Patent No.: US 10,279,329 B2
(45) Date of Patent: May 7, 2019

(54) PYROLYTIC REACTOR AND METHOD OF USING

(71) Applicant: UOP LLC, Des Plaines, IL (US)

(72) Inventors: Rajeswar R. Gattupalli, Buffalo Grove, IL (US); Vinayender Kuchana, Hyderabad (IN); Laura E. Leonard, Western Springs, IL (US); Vighneswara R. Kollati, Krishna District (IN); Aziz Sattar, West Chicago, IL (US); Mohamad R. Mostofi-Ashtiani, Naperville, IL (US); Peter Shafe, Morton Grove, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 15/787,652

(22) Filed: Oct. 18, 2017

(65) Prior Publication Data

US 2018/0036698 A1    Feb. 8, 2018

Related U.S. Application Data

(63) Continuation-in-part of application No. PCT/US2016/037145, filed on Jun. 13, 2016.
(Continued)

(51) Int. Cl.
*C07C 2/78* (2006.01)
*B01J 6/00* (2006.01)
*B01J 3/04* (2006.01)

(52) U.S. Cl.
CPC ............. *B01J 6/008* (2013.01); *B01J 3/044* (2013.01); *C07C 2/78* (2013.01)

(58) Field of Classification Search
None
See application file for complete search history.

(56) References Cited

U.S. PATENT DOCUMENTS 2,958,716 A    11/1960 Lahr et al.
4,724,272 A     2/1988 Raniere et al.
(Continued)

FOREIGN PATENT DOCUMENTS

EP    1413354 A1    4/2004
WO    2015077335 A2    5/2015
WO    2016209648 A1    12/2016

OTHER PUBLICATIONS

Maddalena, "Experimental and Computational Investigation of Light-Gas Injectors in a Mach 4.0 Crossflow", Journal of Propulsion and Power, vol. 22, No. 5 (2006), pp. 1027-1038.
(Continued)

*Primary Examiner* — Philip Y Louie

(57) ABSTRACT

Methods and apparatus to produce alkynes are described. The method includes combusting fuel and an oxidizer in a combustion zone to create a carrier gas stream, which is accelerated to supersonic speed in an expansion zone. A feedstock material is injected into a feedstock injection zone using two or more pluralities of injection nozzles. The injection nozzles are arranged annularly. The carrier gas stream is transitioned from supersonic speed to subsonic speed to create a shockwave in a reaction zone. The reaction zone is directly connected to the feedstock injection zone, and the shockwave is created adjacent to the feedstock injection zone. The carrier gas stream and the feedstock material are simultaneously mixed and reacted.

10 Claims, 2 Drawing Sheets

Related U.S. Application Data

(60) Provisional application No. 62/183,310, filed on Jun. 23, 2015.

(56) References Cited

U.S. PATENT DOCUMENTS

| | | | |
|---|---|---|---|
| 5,300,216 | A | 4/1994 | Hertzberg et al. |
| 5,935,293 | A | 8/1999 | Detering et al. |
| 6,350,394 | B1 | 2/2002 | Ennis et al. |
| 9,370,757 | B2 | 6/2016 | Stevens et al. |
| 9,737,870 | B2 * | 8/2017 | Stevens .................... B01J 3/008 |
| 2014/0058165 | A1 | 2/2014 | Bedard et al. |
| 2014/0058167 | A1 | 2/2014 | Bedard et al. |
| 2014/0058168 | A1 | 2/2014 | Bedard et al. |
| 2014/0058179 | A1 | 2/2014 | Stevens et al. |
| 2015/0165411 | A1 | 6/2015 | Gattupalli et al. |
| 2016/0296904 | A1 | 10/2016 | Knowlen et al. |

OTHER PUBLICATIONS

Tam, "Gaseous and Liquid Injection into High-Speed Crossflows", 43rd AIAA Aerospace Sciences Meeting and Exhibit, Jan. 10-13, 2005, Reno, Nevada, USA.
Search Report dated Oct. 6, 2016 for corresponding PCT Appl. No. PCT/US2016/037145.
Search Report and Written Opinion for corresponding EP application No. 16815049.8, dated Feb. 12, 2019.

* cited by examiner

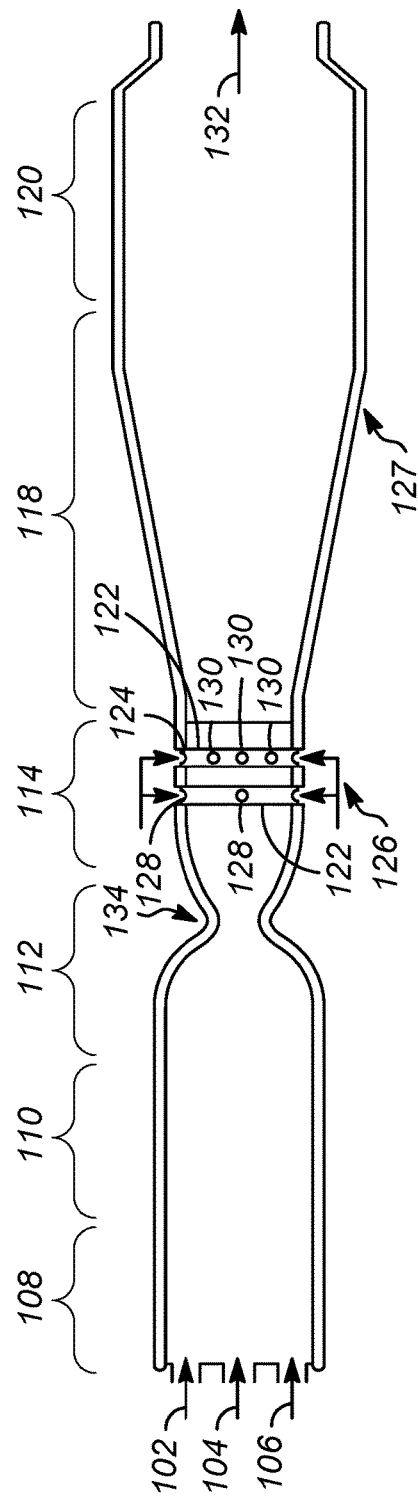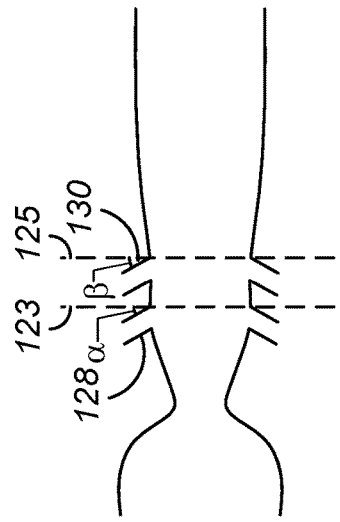

PYROLYTIC REACTOR AND METHOD OF USING

CROSS-REFERENCE TO RELATED APPLICATIONS

This application is a Continuation-In-Part of International Application No. PCT/US2016/037145 filed Jun. 13, 2016 which claims benefit of U.S. Provisional Application No. 62/183,310 filed Jun. 23, 2015, now expired, the contents of which cited applications are hereby incorporated by reference in their entirety.

BACKGROUND OF THE INVENTION

Thermal processing techniques are commonly used to convert feedstock hydrocarbon material to more valuable products. For example, various thermal processing techniques are used to convert methane directly to $C_2$ hydrocarbons, such as acetylene via reaction (1), ethylene via reaction (2), and ethane via reaction (3).

$$2CH_4 \rightarrow C_2H_2 + 3H_2 \qquad (1)$$

$$2CH_4 \rightarrow C_2H_4 + 2H_2 \qquad (2)$$

$$2CH_4 \rightarrow C_2H_6 + H_2 \qquad (3)$$

These reactions are highly endothermic, requiring 377 kJ/mol, 202 kJ/mol, and 65 kJ/mol, respectively. In addition, higher temperatures are generally required to achieve high conversion of the feedstock and high selectivity to the desired product.

One type of thermal processing used in the prior art involves exposing the feedstock to high temperature combustion gases causing the feedstock to pyrolyze into the desired unsaturated product. Many traditional processes involve steam cracking. Other processes involve combustion to generate the necessary temperatures.

The formation of acetylene from methane by thermal processing is difficult because of the relative free energies of formation of methane and acetylene. Acetylene and ethylene can continue reacting to form higher dienes and alkynes such as monovinylacetylene, and aromatic and polyaromatic compounds which can form undesirable tar and soot. Above 800 K, $C_xH_y$ compounds may undergo decomposition into carbon and hydrogen. Below 1500 K, the free energy of formation of methane is above that of acetylene. As such, the formation of methane, the final product of thermodynamic equilibrium, is favored over acetylene between the temperatures of 800 K and 1500 K. Above 1500 K, however, the free energy of formation of acetylene is lower than that of methane. As a result, the formation of acetylene is favored over that of methane. But, as the reactants are cooled below 1500 K, the thermodynamic equilibrium shifts back to methane, and the acetylene produced at the higher temperature will decompose and reform as methane. Acetylene and the other hydrocarbons can continue to react to form aromatic and polyaromatic species. When water and carbon dioxide are present acetylene can react to form carbon monoxide, which is a less valuable product than acetylene. The pyrolitic reaction of methane to form acetylene and other desired hydrocarbons has a high activation energy, while the decomposition reactions of acetylene have lower activation energy. Thus, the formation of acetylene is favored by reacting at high temperatures but with short controlled residence times that minimize consecutive reactions of acetylene with additional acetylene, hydrocarbons and oxygen containing species such as $H_2O$, $CO_2$ and $O_2$.

Certain prior art processes involve combusting a fuel mixture to create a high temperature supersonic carrier stream. A fuel and oxidizer are combusted to produce a hot gas stream at a super-atmospheric pressure and supersonic velocity. Feedstock is injected into the supersonic hot gas stream to initiate the endothermic pyrolysis reactions.

These prior art processes, however, rely on the turbulence of the stream to mix the feedstock within the carrier stream. Increased uniformity of composition and increased uniformity of temperature within the stream during acetylene formation will result in increased conversion and selectivity for the desired product. In prior art processes, feedstock is injected uniformly via a single row of uniform injectors along the wall of the reactor and at a different temperature than the carrier stream. This creates a non-uniform distribution with a stream of highly concentrated, low temperature feedstock alongside the high temperature carrier stream. Prior art reactors therefore included a mixing zone of sufficient length to allow the turbulent flow to mix the feedstock with the carrier stream.

U.S. Publication 2014/0058179 describes a pyrolytic reactor comprising a fuel injection zone, a combustion zone adjacent to the fuel injections zone, an expansion zone adjacent to the combustion zone, a feedstock injection zone comprising a plurality of injection nozzles and disposed adjacent to the expansion zone, a mixing zone configured to mix a carrier stream and feed material and disposed adjacent to the feedstock injection zone, and a reaction zone adjacent to the mixing zone. The plurality of injection nozzles are radially distributed in a first assembly defining a first plane transverse to the feedstock injection zone and in a second assembly transverse to the feedstock injection zone. The mixing zone is needed ensure that combined carrier and feed streams are fully mixed. The presence of this mixing zone will increase the residence time in the reactor and will lead to less desirable products.

Accordingly, there remains a need for an improved pyrolytic reactor having higher conversion and selectivity for the desired product.

SUMMARY OF THE INVENTION

One aspect of the invention is a method to produce alkynes. In one embodiment, the method includes introducing a fuel and an oxidizer into a fuel injection zone; combusting the fuel and the oxidizer in a combustion zone to create a carrier gas stream; and accelerating the carrier gas stream to supersonic speed in an expansion zone. A feedstock material is injected into a feedstock injection zone using at least a first plurality of injection nozzles and a second plurality of injection nozzles, the first plurality of injection nozzles being arranged annularly on a first transverse plane of the feedstock injection zone and the second plurality of injection nozzles being arranged annularly on a second transverse plane of the feedstock injection zone. The carrier gas stream is transitioned from supersonic speed to subsonic speed to create a shockwave in a reaction zone, the reaction zone being directly connected to the feedstock injection zone and the shockwave being created adjacent to the feedstock injection zone. The carrier gas stream and the feedstock material are simultaneously mixed and reacted, and the shockwave helps to mix the carrier gas stream and the feedstock material.

Another aspect of the invention is a pyrolytic reactor. In one embodiment, the pyrolytic reactor includes a fuel injection zone; a combustion zone adjacent to the fuel injections zone; an expansion zone adjacent to the combustion zone; a feedstock injection zone adjacent to the expansion zone, the feedstock injection zone comprising at least a first plurality of injection nozzles and a second plurality of injection nozzles, the first plurality of injection nozzles being arranged annularly on a first transverse plane of the feedstock injection zone and the second plurality of injection nozzles being arranged annularly on a second transverse plane of the feedstock injection zone; and a reaction zone directly connected to the feedstock injection zone.

BRIEF DESCRIPTION OF THE DRAWINGS

FIG. 1 is longitudinal cross section of a pyrolytic reactor having multiple feedstock injection points arranged in two pluralities.

FIG. 2 is longitudinal cross section of a pyrolytic reactor having multiple feedstock injection points arranged in two pluralities showing the injection nozzles.

DETAILED DESCRIPTION OF THE INVENTION

Figure 3A:
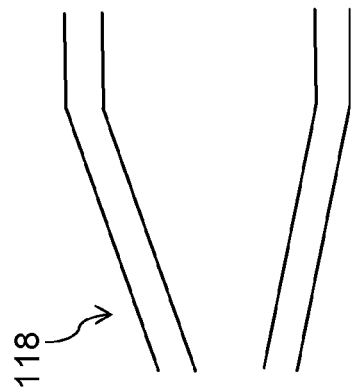
FIGS. 3a, 3b, 3c and 3d show various shapes of a reaction zone in a pyrolytic reactor.

Applicants' apparatus and method provide a pyrolytic reactor capable of injecting feedstock into a carrier stream in a manner that eliminates the mixing zone. It was discovered that the shocks in the reaction zone helps in mixing the feed with the carrier gas thereby eliminating the need for the mixing zone. The shock location can be adjusted by changing the pressure at the exit of the reactor. Mixing and pyrolysis take place simultaneously in the reaction zone which is directly connected to the injection zone, resulting in higher conversion and selectivity for the desired product.

In order to achieve reasonable production to acetylene by thermal processing, the reaction mixture is first heated to a temperature exceeding 1500 K to favor the formation of acetylene. Next, a sufficient amount of reaction enthalpy is provided to satisfy the 377 kJ/mol required for the formation of acetylene. If additional energy is not provided, the endothermic nature of the acetylene formation may drive the temperature below 1500 K. Finally, the reaction mixture is quickly cooled at a rate faster than the rate at which the acetylene can decompose into heavier hydrocarbons such as monovinylacetylene, aromatic and polyaromatic species, tar and soot. This quick cooling process is sometimes referred to as "freezing" the reaction when the amount of acetylene is high. It is desirable to initiate the freezing step at conditions near the maximum acetylene formation (i.e., the point where the rate of formation of acetylene from methane balances the decomposition of acetylene to CO, and heavier hydrocarbons) and to complete the freezing step as quickly as possible to prevent the decomposition of any acetylene.

While the present disclosure is discussed in the context of the pyrolytic conversion of a methane feedstock to acetylene, those skilled in the art will appreciate that the apparatus and methods disclosed herein can be used with other feedstock material to create other products. For example, in one embodiment, Applicants' reactor design and method may be used to convert methane to other higher molecular weight hydrocarbons (other than acetylene), such as ethane, ethylene, or higher molecular weight hydrocarbons (i.e., $C_{2+x}H_y$). In general, Applicants' reactor design and method may be used to facilitate any endothermic reaction that also requires a high temperature for the reaction to occur, such as, without limitation, steam reforming of hydrocarbons, catalytic naphtha cracking, and dehydrogenation to light olefins, such as propylene and ethylene.

Referring to FIG. 1, a longitudinal cross section of a pyrolytic reactor 100 is depicted. In one embodiment, the reactor 100 is tubular (i.e., the transverse cross section is circular). The high temperatures necessary for the formation of acetylene as well as controlled residence time and rapid quenching can be achieved in the pyrolytic reactor 100. Fuel 102 and an oxidizer 106 are injected in the fuel injection zone 108 at the proximal end of reactor 100. In one embodiment, the fuel comprises hydrogen ($H_2$), the oxidizer comprises oxygen, and the ratio of hydrogen to oxygen is a 3/1 molar ratio.

In some embodiments, the fuel 102 and oxidizer 106 are mixed prior to injection into the fuel injection zone 108. In some embodiments, the fuel 102 and oxidizer 106 are injected into the fuel injection zone 108 and mixed by turbulence within the fuel injection zone 108. In some embodiments, a diluent 104, such as steam and/or inert gas, is also injected into the fuel injection zone. In certain embodiments, the diluent is added in an amount less than fifty weight percent (50 wt. %). In certain embodiments, the fuel injection zone is further configured with an additional injector to introduce the diluent into the fuel injection zone.

The fuel and oxidizer are combusted in the combustion zone 110. The combustion heats the carrier gas to a high temperature. In some embodiments, the temperature of the carrier gas reaches up to 2500 K in the combustion zone 110. In other embodiments, the temperature of the carrier gas reaches up to 3000 K in the combustion zone 110. In yet other embodiments, the temperature of the carrier gas reaches up to 3600 K in the combustion zone 110.

The combustion zone 110 is operated at a pressure that is higher than the reaction zone, which propels the carrier gas toward the distal end of the reactor 100 at high velocity. In some embodiments, the velocity of the carrier gas at the distal end of the combustion zone 110 is below supersonic speed (i.e., less than Mach 1).

In an alternative embodiment the feedstock injection zone can be of an annular cross section. The fuel injection zone, combustion zone, expansion zone, and reaction zone may alternatively be either annular or circular. The use of an annular feedstock injection zone reduces the crossflow distance that feed must be injected into the carrier stream. The inner annulus may also be equipped with similar feedstock injection nozzles and can be held in place with struts or secured at the inlet or outlet of the reactor. Struts can have internal channels to allow the flow of feed or coolant. In some embodiments the feedstock injection zone can have other non-circular cross sections that reduce the crossflow distance that feedstock must penetrate into the carrier stream, for example rectangular or elliptical. For the case of a feedstock injection zone with a non-circular cross section the pipe diameter will be understood to mean the hydraulic diameter of the feedstock injection zone.

The subsonic carrier gas enters the expansion zone 112 and flows through a convergent-divergent nozzle 134. The convergent-divergent nozzle 134 transforms a portion of the thermal energy in the carrier stream into kinetic energy, resulting in a sharp increase in velocity of the carrier stream. The velocity of the carrier gas transitions from subsonic (i.e., less than Mach 1) to supersonic (i.e., greater than Mach 1) within the expansion zone 112. In one embodiment, at the distal end of the expansion zone 112, the temperature of the carrier gas is 1500 K to 2500 K and in another embodiment the temperature of the carrier gas is less than 3000 K. In one embodiment, the average velocity of the carrier gas (across a transverse cross section) is greater than Mach 1. In one embodiment, the average velocity of the carrier gas is Mach 2 or above. In one embodiment, the average velocity of the carrier gas is Mach 3 or above.

The methane feedstock is injected into the supersonic carrier gas in the feedstock injection zone 114. In one embodiment, the feedstock is injected at a temperature of 700 K to 1200 K. In one embodiment the feedstock is injected at a temperature of 300 K to 2000 K.

The feedstock is supplied by feed lines 126 and injected via at least two pluralities 122, 124 of injection nozzles 128 and 130, which are arranged in the wall of the feedstock injection zone 114. As shown in FIG. 2, the first plurality 122 defines a first traverse plane 123 through reactor 100, and the second plurality 124 defines a second transverse plane 125 through reactor 100. In some embodiments, there are more than two pluralities of injection nozzles, for example, at least three pluralities. In some embodiments, a diluent, such as steam and/or an inert gas, can be injected using the injection nozzles. In some embodiments, the diluent can be injected using the first plurality of injection nozzles, while the feedstock is injected using the second plurality. In other embodiments, the diluent and a portion of the feedstock are injected using the first plurality, and the rest of the diluent is injected using the second plurality. If more than two pluralities of injection nozzles are included, the diluent and feedstock using one or two pluralities, and the remainder of the feedstock can be divided among the rest of the pluralities.

In one embodiment, the nozzles 128 and 130 are disposed directly in the wall of the feedstock injection zone 114. In one embodiment, the nozzles 128 and 130 are mounted in a circular structure that is in line with the wall of the reactor 100 to form the feedstock injection zone 114. In one embodiment, the nozzles 128 and 130 are mounted in elliptical or other structure that is in line with the wall of the reactor 100 to form the feedstock injection zone 114.

In one embodiment, the first plurality 122 comprises at least three (3) nozzles. In certain embodiments, the first plurality 122 comprises more than three nozzles, and in others fewer than three nozzles. In certain embodiments the nozzles of the first plurality 122 are equally spaced around the perimeter of the feedstock injection zone 114.

In certain embodiments, the second plurality 124 comprises at least three (3) nozzles, although there can more or less than three nozzles. In certain embodiments, the nozzles of the second plurality 124 are equally spaced around the perimeter of the feedstock injection zone 114.

The first and second pluralities 122 and 124 can comprise the same number of injection nozzles, the first plurality 122 can comprise more injection nozzles than the second plurality 124, or the second plurality 124 can comprise more nozzles than the first plurality 122. In some embodiments, the number of nozzles in a given plurality may be 1 to 200.

The first and second pluralities 122 and 124 of injection nozzles can be arranged in the same annular positions, or they can be offset from each other.

When there are at least three pluralities, all of the pluralities can have the same number of injection nozzles, or one or more can have a different number of injection nozzles. All of the pluralities can be arranged in the same annular positions, or one or more can be arranged in different annular positions.

In one embodiment, each of the nozzles 128 in the first plurality 122 is configured to inject the feedstock into the carrier stream to a depth of ⅓ the distance to the centerline of the feedstock injection zone 114 (i.e., a radial depth of ⅓ the distance to the radial midpoint of the feedstock injection zone) and each of the nozzles 130 in the second plurality 124 is configured to inject the feedstock into the carrier stream to a radial depth of ⅔. The radial depth of penetration into the carrier stream is a function of the angle at which the feedstock is injected into the carrier stream, the flow rate at each nozzle, the diameter of the nozzle and the velocity of the carrier stream through the feedstock injection zone 114.

As would be appreciated by those skilled in the art, while the arrangement of nozzles are described as aligned in transverse planes (i.e., perpendicular to the longitudinal axis of the reactor 100), the nozzles may be distributed in any other manner within the feedstock injection zone 114 to achieve the angular distribution (i.e., different angular points at a given radial depth) and radial distribution (i.e., different radial depths at a given angular point) in the carrier stream. Or, the nozzles 128 may be staggered at different locations on the feedstock injection zone 114. For example, instead of being arranged in transverse planes, the nozzles 128 may be arranged in a plane offset from the perpendicular by an angle α, as shown in FIG. 2. The injection nozzles 128 and 130 form an angle α with respect to the transverse planes 123, 125 in the range of 0° to 90°, or 0° to 80°, or 0° to 70°.

In different embodiments, the injection nozzles 128 and 130 are jets, angled jets, aeroramp jets, ramp jets, strut jets, cascade jets, diamond jets, slotted holes, and annular slots, or combinations thereof.

The radial depth of penetration of the jet into the carrier stream can be determined by a number of means known to those skilled in the art, such as mathematical correlations, computational fluid dynamic modeling, experimental measurement of concentration, temperature, density. Equation 1 is an example of a mathematical correlation in which a, b, c and d are positive constants, $M_j$ is the Mach number of the jet, $d_j$ is the throat diameter of the injector, $(\rho v^2)_j$ is the momentum of the jet at the throat of the nozzle, $(\rho v^2)_c$ is the momentum of the carrier stream and $\Theta$ is the angle of the jet from the downstream wall. The throat of the nozzle is defined as the portion of the nozzle that has the minimum cross sectional area. The radial depth of penetration of the jet into the carrier stream is also impacted by the type of injector. For example an aeroramp injector (examples of which are described in the JOURNAL OF PROPULSION AND POWER, Vol. 22, No. 5, September-October 2006, pg. 1027 to 1038 and paper AIAA 2005-301 from the American Institute of Aeronautics and Astronautics) can be used to provide deeper penetration of the jet with less pressure loss. For an injector that is not a single circular nozzle, for example an aeroramp injector, the throat diameter of the injector, $d_j$, is taken to be the diameter of a circle with the combined throat area of the individual jets making up the aeroramp. For example, if an aeroramp has 5 individual jets all with the same throat diameter, then $d_j$ would be the square root of 5 times the diameter of the throat diameter of the individual jets making up the aeroramp injector. In one embodiment aeroramp jets are used for the assembly of jets that are designed to have the furthest penetration.

$$\frac{y}{d_j} = a \left[ \frac{(\rho v^2)_j}{(\rho v^2)_c} \right]^b M_j^c \Theta_d \qquad \text{Equation (1)}$$

The injection of the feedstock along the perimeter of the feedstock injection zone 114 and at multiple transverse planes 123, 125 result in increased mixing of the feedstock with the carrier stream.

In some embodiments, the nozzles within one assembly may inject feedstock at different radial depths.

In one embodiment, the feedstock is fully injected between 0.5 and 10 pipe diameters (i.e., inner diameter of the injection zone) downstream of the first injection location. In other words, in FIG. 1, the distance between the first plurality 122 (the first injection point upstream) and the second plurality 124 (the last injection point downstream) is between 0.5 and 10 pipe diameters. In other embodiments, the feedstock is fully injected between 0.5 and 6 pipe diameters downstream of the first injection location or between 1 and 5 pipe diameters, or 2 and 5 pipe diameters. In yet other embodiments, the feedstock is fully injected less than 1 pipe diameter downstream of the first injection location.

The feedstock injection zone 114 is directly connected to the reaction zone 118 eliminating the mixing zone from the prior art.

The transverse cross section of the reactor 100 increases in the reaction zone 118 due to angled wall 127.

In some embodiments, the velocity of the mixed stream remains at supersonic velocities within the reaction zone 118. Back pressure is used in the reaction zone to create a shock wave that converts the kinetic energy of the carrier gas back into thermal energy to increase the temperature and cause the methane to react by pyrolysis. Adjusting the pressure at the exit of the reactor will help in creating shocks in the reaction zone, which causes a reduction in the velocity of the carrier stream, converting a portion of the kinetic energy in the stream into thermal energy. The product mixture is then reduced to subsonic flow and quenched in quench/recovery zone 120.

Shocks will help in transitioning the velocity of the mixed stream from supersonic to subsonic within the reaction zone 118, and the location of the shock can be adjusted by changing the pressure at the exit of the reactor. The reactor exit pressure can be adjusted to achieve the shock immediately after the injection zone, which helps in mixing the feed with the carrier gas and thereby eliminating the need for the mixing zone. The presence of the shockwave results in a nearly instantaneous increase in the static pressure and temperature of the mixed stream. In various embodiments, the temperature of the mixed stream immediately upstream of the shockwave is 1500 K to 2000 K, as compared to 1800 K to 2300 K immediately downstream of the shockwave. The conditions in the mixed stream downstream of the shockwave are favorable to the formation of acetylene.

In some embodiments, a shock train is formed at the point where the stream transitions from supersonic to subsonic flow. A shock train is a series of weak shockwaves that propagate downstream from the supersonic to subsonic transition point. Whereas a single shockwave will heat the mixture nearly instantaneously (at the location of the shockwave), a shock train will heat the mixture more gradually. Each shockwave in the shock train will increase the temperature of the stream.

The mixed stream is increased to a temperature sufficient to favor the formation of acetylene and to provide enough energy to satisfy the endothermic reaction.

Figure 3B:
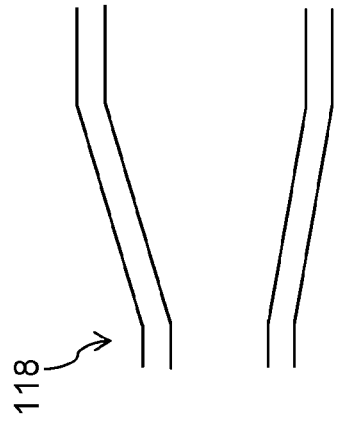
Figure 3C:
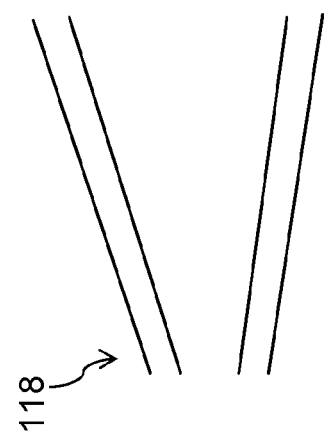
Figure 3D:
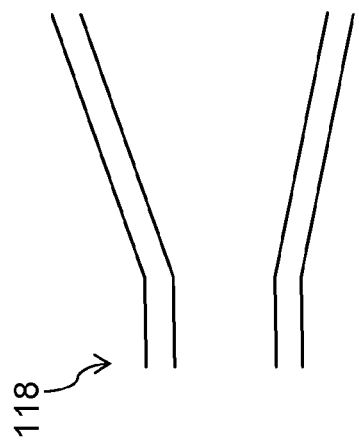

The shape of the reaction zone 118 can be one of diverging, diverging flat, flat diverging or flat diverging flat as shown in FIG. 3a, FIG. 3b, FIG. 3c and FIG. 3d respectively. Applicants have found that any of the above shape as shown in FIG. 3a, FIG. 3b, FIG. 3c and FIG. 3d are less sensitive to back pressure as compared to a completely flat shaped or cylindrical reaction zone. Further, much lower reactor lengths can be used to obtain yields comparable to the completely flat shaped or cylindrical reaction zone. As the differential area (dA/dx) in the reaction zone 118 having a diverging component as shown in FIGS. 3a, 3b, 3c and 3d will be more, hence differential pressure (dP/dx) would also be more as compared to the completely flat shaped or cylindrical reaction zone. Hence, shock location would move lesser for ducts with larger wall angles for a change in back pressure.

In one embodiment, the product stream exits the reaction zone 118 and enters the quench/recovery zone 120 to rapidly cool the product stream. In one embodiment, the quenching zone 120 comprises at least one injection nozzle to spray the product stream with water. The product stream is recovered at the distal end of the reactor 100 as indicated by 132.

In an alternative embodiment the feedstock injection zone can be of an annular cross section. The fuel injection zone, combustion zone, expansion zone, and reaction zone may alternatively be either annular or circular. The use of an annular feedstock injection zone reduces the cross flow distance that feed must be injected into the carrier stream. The inner annulus may also be equipped with similar feedstock injection nozzles and can be held in place with struts or secured at the inlet or outlet of the reactor. Struts can have internal channels to allow the flow of feed or coolant. In some embodiments the feedstock injection zone can have other non-circular cross sections that reduce the cross flow distance that feedstock must penetrate into the carrier stream, for example rectangular or elliptical. For the case of a feedstock injection zone with a non-circular cross section the pipe diameter will be understood to mean the hydraulic diameter of the feedstock injection zone.

In some embodiments, the first and second pluralities of injector nozzles can be assemblies which are separate components disposed in the body of reactor 100, or assemblies integral with the body of reactor 100.

The performance of each nozzle is configured to deliver the feedstock to the target location for a given carrier stream velocity. In certain embodiments, the penetration depth of each nozzle is monitored and dynamically adjusted to maintain the desired penetration depth.

In certain embodiments, a feedstock target radial penetration depth for each injection nozzle in the plurality of injection nozzles is different from a feedstock target radial penetration depth for all other injection nozzles in the plurality of injection nozzles. In certain embodiments, a jet diameter of injection nozzles in the first assembly is larger than a throat diameter of the nozzles in the second assembly. In certain embodiments, the injection pressure of the nozzles in the first assembly is greater than the injection pressure of the nozzles in the second assembly.

In certain embodiments, the first plane of feed injection nozzles is situated within an expanding nozzle. In certain embodiments, the second plane of feed injection nozzles is situated within an expanding nozzle. In certain embodiments, the third plane of feed injection nozzles is situated within an expanding nozzle.

This invention is described in preferred embodiments in the following description with reference to the FIGURES, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of the invention may be combined in any suitable manner in one or more embodiments.

SPECIFIC EMBODIMENTS

While the following is described in conjunction with specific embodiments, it will be understood that this description is intended to illustrate and not limit the scope of the preceding description and the appended claims.

A first embodiment of the invention is a method to produce an alkyne, comprising introducing a fuel and an oxidizer into a fuel injection zone; combusting the fuel and the oxidizer in a combustion zone to create a carrier gas stream; accelerating the carrier gas stream to supersonic speed in an expansion zone; injecting a feedstock material into a feedstock injection zone using at least a first plurality of injection nozzles and a second plurality of injection nozzles, the first plurality of injection nozzles being arranged annularly on a first transverse plane of the feedstock injection zone and the second plurality of injection nozzles being arranged annularly on a second transverse plane of the feedstock injection zone; transitioning the carrier gas stream from supersonic speed to subsonic speed to create a shockwave in a reaction zone, the reaction zone being directly connected to the feedstock injection zone and the shockwave being created adjacent to the feedstock injection zone; and simultaneously mixing and reacting the carrier gas stream and the feedstock material, the shockwave helping to mix the carrier gas stream and the feedstock material. An embodiment of the invention is one, any or all of prior embodiments in this paragraph up through the first embodiment in this paragraph, wherein the first plurality of injection nozzles comprises at least three injection nozzles and the second plurality of injection nozzles comprises at least three injection nozzles. An embodiment of the invention is one, any or all of prior embodiments in this paragraph up through the first embodiment in this paragraph, wherein the first and second plurality of injection nozzles comprise the same number of injection nozzles and wherein the first and second plurality of injection nozzles are arranged at the same annular positions. An embodiment of the invention is one, any or all of prior embodiments in this paragraph up through the first embodiment in this paragraph, wherein the feedstock injection zone has a pipe diameter, and the first transverse plane is spaced from the second transverse plane by a distance of between 0.5 to 6 injection zone pipe diameters. An embodiment of the invention is one, any or all of prior embodiments in this paragraph up through the first embodiment in this paragraph, wherein the feedstock injection zone comprises a third plurality of injection nozzles arranged annularly on a third transverse plane of the feedstock injection zone. An embodiment of the invention is one, any or all of prior embodiments in this paragraph up through the first embodiment in this paragraph, wherein 10 wt % to 50 wt % of the feedstock material is introduced into the first plurality of injection nozzles and 50 wt % to 90 wt % of the feedstock material is introduced into the second plurality of injection nozzles. An embodiment of the invention is one, any or all of prior embodiments in this paragraph up through the first embodiment in this paragraph, further comprising introducing a diluent into the feedstock injection zone. An embodiment of the invention is one, any or all of prior embodiments in this paragraph up through the first embodiment in this paragraph, wherein the diluent is introduced using the first plurality of injection nozzles. An embodiment of the invention is one, any or all of prior embodiments in this paragraph up through the first embodiment in this paragraph, wherein the diluent and a first portion of the feedstock material are introduced using the first plurality of injection nozzles, and a second portion of the feedstock material is introduced using the second plurality of injection nozzles. An embodiment of the invention is one, any or all of prior embodiments in this paragraph up through the first embodiment in this paragraph, wherein the diluent is introduced using the first plurality of injection nozzles, and the feedstock material is introduced using the second plurality of injection nozzles. An embodiment of the invention is one, any or all of prior embodiments in this paragraph up through the first embodiment in this paragraph, further comprising reducing a velocity of the carrier gas stream in the reaction zone to convert kinetic energy to thermal energy. An embodiment of the invention is one, any or all of prior embodiments in this paragraph up through the first embodiment in this paragraph, wherein the first plurality of injection nozzles has an angle relative to the first transverse plane in a range of 0° to less than 90° and the second plurality of injection nozzles has an angle relative to the second transverse plane in a range of 0° to 90°. An embodiment of the invention is one, any or all of prior embodiments in this paragraph up through the first embodiment in this paragraph, wherein the angle of the first plurality of injection nozzles is different from the angle of the second plurality of injection nozzles. An embodiment of the invention is one, any or all of prior embodiments in this paragraph up through the first embodiment in this paragraph, wherein each injection nozzle of the first and second plurality of injection nozzles is selected from the group consisting of jets, angled jets, aeroramp jets, ramp jets, strut jets, cascade jets, diamond jets, slotted holes, and annular slots, or combinations thereof.

A second embodiment of the invention is a method of pyrolytic reactor, comprising a fuel injection zone; a combustion zone adjacent to the fuel injections zone; an expansion zone adjacent to the combustion zone; a feedstock injection zone adjacent to the expansion zone, the feedstock injection zone comprising at least a first plurality of injection nozzles and a second plurality of injection nozzles, the first plurality of injection nozzles being arranged annularly on a first transverse plane of the feedstock injection zone and the second plurality of injection nozzles being arranged annularly on a second transverse plane of the feedstock injection zone; and a reaction zone directly connected to the feedstock injection zone. An embodiment of the invention is one, any or all of prior embodiments in this paragraph up through the second embodiment in this paragraph, wherein the first plurality of injection nozzles comprises at least three injection nozzles and the second plurality of injection nozzles comprises at least three injection nozzles. An embodiment of the invention is one, any or all of prior embodiments in this paragraph up through the second embodiment in this paragraph, wherein the first and second plurality of injection nozzles comprise the same number of injection nozzles and wherein the first and second plurality of injection nozzles are arranged at the same annular positions. An embodiment of the invention is one, any or all of prior embodiments in this paragraph up through the second embodiment in this paragraph, wherein the feedstock injection zone comprises a third plurality of injection nozzles arranged annularly on a third transverse plane of the feedstock injection zone. An embodiment of the invention is one, any or all of prior embodiments in this paragraph up through the second embodiment in this paragraph, wherein the first plurality of injection nozzles has an angle relative to the first transverse plane in a range of 0° to 90° and the second plurality of injection nozzles has an angle relative to the second transverse plane in a range of 0° to 90°. An embodiment of the invention is one, any or all of prior embodiments in this paragraph up through the second embodiment in this paragraph, wherein each injection nozzle of the first and second plurality of injection nozzles is selected from the group consisting of jets, angled jets, aeroramp jets, ramp jets, strut jets, slotted holes, and annular slots.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

The invention claimed is:

1. A method to produce an alkyne, comprising:
    introducing a fuel and an oxidizer into a fuel injection zone;
    combusting the fuel and the oxidizer in a combustion zone to create a carrier gas stream;
    accelerating the carrier gas stream to supersonic speed in an expansion zone;
    injecting a feedstock material into a feedstock injection zone using at least a first plurality of injection nozzles and a second plurality of injection nozzles, the first plurality of injection nozzles being arranged annularly on a first transverse plane of the feedstock injection zone and the second plurality of injection nozzles being arranged annularly on a second transverse plane of the feedstock injection zone;
    transitioning the carrier gas stream from supersonic speed to subsonic speed to create a shockwave in a reaction zone, the reaction zone being directly connected to the feedstock injection zone and the shockwave being created adjacent to the feedstock injection zone; and
    simultaneously mixing and reacting the carrier gas stream and the feedstock material to form the alkyne, the shockwave helping to mix the carrier gas stream and the feedstock material.

2. The method of claim 1, wherein the first plurality of injection nozzles comprises at least three injection nozzles and the second plurality of injection nozzles comprises at least three injection nozzles.

3. The method of claim 1, wherein the first and second plurality of injection nozzles comprise the same number of injection nozzles and wherein the first and second plurality of injection nozzles are arranged at the same annular positions.

4. The method of claim 1, wherein the feedstock injection zone has a pipe diameter, and the first transverse plane is spaced from the second transverse plane by a distance of between 0.5 to 6 injection zone pipe diameters.

5. The method of claim 1, wherein the feedstock injection zone comprises a third plurality of injection nozzles arranged annularly on a third transverse plane of the feedstock injection zone.

6. The method of claim 1, wherein 10 wt % to 50 wt % of the feedstock material is introduced into the first plurality of injection nozzles and 50 wt % to 90 wt % of the feedstock material is introduced into the second plurality of injection nozzles.

7. The method of claim 1 further comprising introducing a diluent into the feedstock injection zone.

8. The method of claim 1, further comprising reducing a velocity of the carrier gas stream in the reaction zone to convert kinetic energy to thermal energy.

9. The method of claim 1, wherein the first plurality of injection nozzles has an angle relative to the first transverse plane in a range of 0° to less than 90° and the second plurality of injection nozzles has an angle relative to the second transverse plane in a range of 0° to 90°.

10. The method of claim 1, wherein each injection nozzle of the first and second plurality of injection nozzles is selected from the group consisting of jets, angled jets, aeroramp jets, ramp jets, strut jets, cascade jets, diamond jets, slotted holes, annular slots, and combinations thereof.

* * * * *